July 4, 1972 G. MERRILL Plant Pat. 3,230
PEACH TREE
Filed Jan. 7, 1971
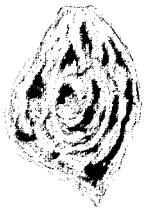
GRANT MERRILL
INVENTOR
Virgil L. Gerard
ATTORNEY

United States Patent Office

Plant Pat. 3,230
Patented July 4, 1972

3,230

PEACH TREE

Grant Merrill, Tulare County, Calif.
(416 N. Anderson Road, Exeter, Calif. 93221)

Filed Jan. 7, 1971, Ser. No. 104,821
Int. Cl. A01h *5/03*
U.S. Cl. Plt.—43 1 Claim

The present invention relates to a peach tree and more particularly to a new and distinct variety thereof broadly characterized by a vigorous tree and regular bearing of firm fruit which matures very late and has 10% to 50% of its skin surface covered with bright red blush upon an under color of bright yellow, these being good characteristics for shipping, and bright yellow flesh with a small amount of light red around the stone, making it a good fruit for commercial freezing.

The instant variety most nearly resembles Halloween II (U.S. Plant Patent No. 1,472) but is distinguished therefrom by reason of its having more red on the skin with a brighter yellow under color, and flesh that is firmer and of brighter yellow color with less red, and that red being a brighter red.

I discovered the present variety of peach on the farm formerly owned by me at Red Bluff, Tehama County, Calif., by growing seeds from a seedling, numbered 29–21C, which grew from seeds derived from a tree which resulted from open pollenation of a J. H. Hale (unpatented and a seedling resulting from a cross of J. H. Hale and Levi Cling (unpatented). This breeding may be expressed as [[P. H. Hale×(J. H. Hale ×Levi Cling) o.p.] ×o.p.] o.p.

The instant variety has been asexually reproduced by budding and grafting a test tree on my farm at Exeter, Tulare County, Calif. and on test plots on farms in northern Tulare County, Calif. In each case, the present variety was exactly the same as the original fruit and tree (seedling E28–7SW).

The accompanying drawing is an oil painting of a characteristic mature fruit of the subject peach variety showing the shape and skin color, and by means of a fruit divided on its suture, showing the characteristic flesh color, when fresh, and the shape of the stone.

Referring now more specifically to the pomological characteristics of this new and distinct variety of peach tree, the following has been observed under the ecological conditions prevailing in Tulare County, Calif., and is an outline description thereof. All major color plate identifications are by reference to Maerz and Paul's Dictionary of Color, First Edition.

*Tree*

Size: large.
Trunk: medium size, shaggy, gray in color.
Branches: gray and shaggy when old, brown and smoother when young; medium size.
Lenticels: medium in size, numerous.
Twigs: long, with long internodes, green to red-brown in color, smooth.

*Leaves*

(Selceted from midportion of new growth when 18 to 24 inches in length)

Shape: lanceolate, tip acuminate.
Size: medium to large size, length 5½ to 7½ inches, width 1¾ to 2 inches.
Color: dark green on upper surfaces, lighter green under surface, veins very light yellow green color.
Class: (Meader & Blake: Proceedings of the American Society for Horticultural Science, volume 37, page 203) Class Two.
Margin: glandular.
Petiole: medium size, generally about ½ inch long.

Glands: reniform, on petiole and lower parts of leaf.
Stipules: present on young leaves, dropping off early.
Character: deciduous.

*Flowers*

Blooms: large, showy, light pink.
Date of Bloom: medium early, about with Halloween II (U.S. Plant Patent No. 1,472).
Pollen: abundant.

*Fruit*

(Described at maturity—1970 growing season)

Season of ripening: firm ripe about October 1.
Size: large and globose, but variable in size and shape, generally very small tip.
Dimensions: axial diameter, 2½ to 3½ inches; transverse in suture plane, 2½ to 3⅝ inches; and at right angle to suture plane, 2½ to 3⅝ inches.
Suture: inconspicuous, usually very slight ridge, extends from base toward and beyond apex but discontinues at apex; has slight depression beyond pistil point.
Dorsal surface: rounded.
Cavity: medium size, elongated in suture plane with suture showing on both sides; depth ¼ to ½ inch, breadth ¾ to 1 inch; and markings the same as the skin surface.
Base: retuse.
Apex: mucronate.
Pistil point: apical, very short to depressed.
Stem: short, ⅛ to ¼ inch long, ⅛ inch or less in diameter.
Skin color: light side, lightest yellow 9–I–3 to medium yellow 9–K–3 to darkest yellow 9–K–9, overlaid with red spots 1–G–12; darkest side, yellow 9–L–3 overlaid with lightest red 1–I–11 to "Venetian Rose" 5–L–1 to darker "Red Cross" 4–L–6.
Skin thickness: medium, tenacious to flesh.
Skin pubescence: scant.

*Flesh*

Color: yellow 9–L–3 with bright red in small amounts next to stone 1–G–12 to 5–L–1, with stone cavity light "Castilian Red," 1–L–10.
Amygdalin: moderate.
Juice: rich.
Texture: meaty.
Fibers: moderate, tender.
Ripens: evenly.
Flavor: mild, delicate.
Firmness: throughout.
Aroma: distict.
Eating quality: good.
Freeizng quality: good.

*Stone*

Color: when freshly cut, from light "Paloma" red 12–A–9 to dark red 48–L–1 with stain of "Venetian Rose" 5–L–1.
Tenacity to flesh: from ripe to soft ripe, completely free.
Fibers: wanting.
Size: medium; length, 1⅜ to 1⅝ inches; width, 15/16 to 1 3/16 inches; thickness ⅝ to ⅞ inches.
Form: obovate, tip acuminate; base, some straight, some oblique; hilum, oval.
Surface: irregularly furrowed and pitted throughout.
Ventral edge: thick, small grooves throughout.
Dorsal edge: raised with deep grooves, discontinuous or reduced near apex on some.
Tendency to split: slight.

*Use*

Shipping: nearby or long distance, general market.
Storage: good.
Commercial freezing: good.

Although the new variety of peach tree posseses the described characteristics under the ecological conditions prevailing in Tulare and Tehama Counties, Calif., having been first observed near Red Bluff, Tehama County, Calif., it is to be understood that variations of the usual magnitude in characteristics incident to the growing conditions, fertilization, pruning and pest control are to be expected.

Having thus described and illustrated my new variety of peach tree, what is claimed is:

1. A new and distinct variety of peach tree substantially as illustrated and described and being characterized by a vigorously growing tree regularly bearing fruit which matures very late and has 10% to 50% of its skin surface covered with a bright red blush with an under color of bright yellow, and with firm flesh, these being good characteristics for shipping, and by bright yellow flesh with a small amount of light red around the stone, these being good characteristics for commercial freezing, and which most nearly resembles the Halloween II (U.S. Plant Pat. No. 1,472), but is an improvement on that variety by its higher skin color and its firmer and brighter yellow flesh color with less but brighter red next to the stone, thus providing better shipping and freezing qualities.

No references cited.

ROBERT E. BAGWILL, Primary Examiner